United States Patent [19]
Touryanski et al.

[11] Patent Number: 6,041,098
[45] Date of Patent: Mar. 21, 2000

[54] X-RAY REFLECTOMETER

[76] Inventors: Alexander G. Touryanski; Alexander V. Vinogradov; Igor V. Pirshin, all of X-Ray Optics Group, P.N. Lebedev Physical Institute, Leninsky Prospekt, 53, Moscow, Russian Federation, 117924

[21] Appl. No.: 09/020,583

[22] Filed: Feb. 2, 1998

[30] Foreign Application Priority Data

Feb. 3, 1997 [RU] Russian Federation ........... 971016153

[51] Int. Cl.$^7$ .................................................. G01N 23/20
[52] U.S. Cl. ............................... 378/70; 378/70; 378/79; 378/88
[58] Field of Search ................. 378/85, 84, 88, 378/89, 147, 70, 71, 79, 81

[56] References Cited

U.S. PATENT DOCUMENTS

| | | | |
|---|---|---|---|
| 3,702,933 | 11/1972 | Fields et al. | |
| 4,884,290 | 11/1989 | Tamura et al. | 378/83 |
| 5,509,043 | 4/1996 | Van Der Sluis | 378/85 |
| 5,761,256 | 6/1998 | Inoue et al. | 378/84 |

OTHER PUBLICATIONS

O. Renner, "Density Measurements of Thin Geranium Films by Total Reflection of X-Rays," Czech J. Phys. 1972, 5pp., Prague.

Gerard M. Zorn, "The New Siemens X-Ray Reflectometer", Analytical Application Note, Jan., 1994, 2pp., 337 Siemans AG, Munich, Germany.

O.J. Guentert, "Study of the Anomalous Surface of X Rays," Journal of Applied Physics, Apr., 1965, 2pp., vol. 36, No. 4, USA.

L.G. Parratt, "Surface Studies of Solids by Total Reflection of X–Rays," Physical Review, Jul. 15, 1954, 1p., vol. 95, No. 2., USA.

R. Barchewitz, "X–ray photoabsorbption of solids by specular relfection," J. Phys. C:Solid State Phys., 1978, 9pp., vol. 11, The Institute of Physics, Great Britian.

*Primary Examiner*—David V. Bruce
*Assistant Examiner*—Michael J. Schwartz
*Attorney, Agent, or Firm*—Ian F. Burns

[57] ABSTRACT

The present invention relates to X-ray devices for the investigation of material structure, density and geometry of reflected surfaces by measuring reflected, diffracted or scattered radiation. These X-ray optical devices are especially useful for measuring polished surfaces with large reflective areas which are used in the electronics and the computer industry (wafers, memory discs), high precision mechanics and optics. The present invention describes a device which increases the accuracy and efficiency in which X-ray reflectometry measurements can be made in different parts of the X-ray spectral region. The main technical advantages of the invention are a two-fold reduction in the ultimate error of angular measurements in different spectral regions, and a decrease in the random errors associated with the intensity measurements that are observed which are due in part to a drift in the electric parameters of the device. Another technical advantage is the reduction in the measurement time for the study of single samples.

13 Claims, 2 Drawing Sheets

X-RAY REFLECTOMETER

BACKGROUND OF THE INVENTION

The present invention relates to X-ray devices for the investigation of material structure, density and geometry of reflected surfaces by measuring reflected, diffracted or scattered radiation. These X-ray optical devices are especially useful for measuring polished surfaces with large reflective areas which are used in the electronics and the computer industry (wafers, memory discs), high precision mechanics and optics.

An X-ray reflectometer has previously been described [1] that has the following components: a source of polychromatic X-ray radiation; the means for X-ray beam collimation; a sample holder with provisions for rotating the holder around its own axis; an arm support with a means for rotation around an axis coinciding with the sample holder axis; a means for measuring the rotation angles of the sample holder and arm support; a crystal-monochromator; and a detector [1]. In this device [1], the monochromator is located between the X-ray source and the sample holder. Therefore, to switch the measurement to a new spectral region it is necessary to rotate the monochromator and other elements of this device corresponding a new Bragg angle. These elements are the X-ray source, and the means for making the measurements of the rotation angles of the sample holder, arm support etc., which are usually the parts of a precise opto-mechanical goniometer. The change in relative positions of the elements of the X-ray device causes misalignment of the device and requires accurate adjustment, which is a time consuming procedure, which takes a much longer time than that needed for the actual measurement of the sample parameters. For this reason, the measurements of spectral dependence of real and imaginary parts of the refractive index and scattering diagram are inefficient and poorly reproducible. These measurements are regularly used for the determination of density and composition of the bulk and surface layer of a sample. The above mentioned shortcomings of this device [1] reduce considerably the accuracy and reliability of the obtained data.

Also known in the art is an X-ray reflectometer containing a source of polychromatic X-rays, a sample holder with provisions for rotating the holder around its own axis, an arm support for which the rotation around the same axis is provided, a means for measuring the rotation angles of the sample holder and arm support, crystal monochromators, a crystal analyzer and a detector [2]. The crystal-monochromator is placed between the radiation source and the sample holder, and the crystal-analyzer is placed behind the sample holder on the path of the X-ray beam. A working region of the spectrum is cut out from the primary radiation by means of a monochromator, and the angles of reflection of the reflected or scattered radiation in respect of the direction of a primary monochromatic beam are measured by means of the rotation of the crystal-analyzer around its own axis. A perfect crystal whose diffraction angle does not change due to displacement of a radiation region is used as an analyzer. This makes it possible to eliminate the dependence of angular measurements on the position and dimensions of a sample in a beam. However, the installation of the second crystal makes the transmission of X-ray radiation considerably lower. Moreover, the changing of the spectral range (similar to the device described in reference [1]) requires long and complex adjustment.

In yet another X-ray reflectometer [3], the reflectometer comprises a source of polychromatic X-rays, a means of collimating of an X-ray beam, a sample holder, an arm support, a means of rotation of said sample holder and said arm support about a predetermined axis, tunable to a predetermined spectral band, a means of monochromatisation and detection of scattered, reflected or diffracted X-rays positioned on said arm support.

The main drawback of this arrangement is the random errors that are generated in measurements of different parts of the spectrum. These errors are due to the fact that such measurements, which are made by means of the device [3], should be performed successively after tuning the device for a new part of the spectrum. As a result, the conditions of data recording are changed due to the drift of the electric parameters of an X-ray source, the detector, and data processing channel during adjustment and repeated measurements. As a rule, this leads to uncontrollable errors connected with variations of the X-ray spectrum, the amplitude of the detector pulses, the level of noise, and the gain coefficient of the data processing channel. The other source of error is the non-reproducibility of the primary angular coordinates of the sample surface in respect to the beam after adjustment to a new part of the spectrum. The angular error is mainly due to the uncontrollable displacement of the sample during its repeated input into an X-ray beam, and the finite accuracy of angular measurements by means of a goniometric device.

In the described device [3], the rotation of only finite elements of the X-ray reflectometer (monochromator and detector) is needed to adjust the device to a new part of the spectral region. However, if a narrow part of the X-ray spectrum has been chosen, then it will take a considerable amount of time to adjust the monochromator and the detector. The total time needed for control and measurement of a single sample is made up of the measurement time (tm) in each part of the spectrum, the adjustment time (ta) of the measurement system, and the definition of initial angular coordinates (tk). Normally, ta+tk>>tm. Therefore, the efficiency in which measurements are made with such an X-ray reflectometer [3] is quite low.

SUMMARY OF THE INVENTION

The present invention describes a device which increases the accuracy and efficiency in which X-ray reflectometry measurements can be made in different parts of the X-ray spectral region. The main technical advantages of the invention are a two-fold reduction in the ultimate error of angular measurements in different spectral regions, and a decrease in the random errors associated with the intensity measurements that are observed which are due in part to a drift in the electric parameters of the device. Another technical advantage is the reduction in the measurement time for the study of single samples.

DETAILED DESCRIPTION OF PREFERRED EMBODIMENTS OF THE INVENTION

The invention, consists of an X-ray reflectometer comprising a source of polychromatic X-rays, a means of collimating of an X-ray beam, a sample holder, an arm support, a means of rotation of said sample holder and said arm support about a predetermined axis, tunable to predetermined spectral bands, a means of monochromatisation and detection of scattered, reflected or diffracted X-rays positioned on said arm support, wherein said means of monochromatization are formed by a row of monochromators positioned in a radial direction with respect to predetermined axes of rotation, said monochromators and corresponding detection means are simultaneously tunable to different predetermined spectral bands and every said monochromator positioned before the last one in a said row is semitransparent in predetermined spectral bands.

The technical specifications of said X-ray reflectometer are also enhanced by the fact that the first monochromator is made in the form of a plate satisfying the condition:

$$0.05 < \mu d/\sin(\theta) < 0.5 \quad (1)$$

where $\mu$ is the linear coefficient of attenuation of the radiation transmitted through the plate, for the part of spectrum being analyzed, d is the plate thickness, $\theta$ is the Bragg angle for a part of the spectrum reflected by the plate. The above technical results are also achieved due to the fact that the first monochromator is made of a pyrolytic graphite.

The composition and location of the elements of the X-ray reflectometer, according to the claimed invention, provide the singling out of two spectral regions in the recorded radiation, and their consequent independent registration by two detecting channels. This allows one to perform simultaneous measurements of the angular dependencies of the reflection and transmission coefficients, as well as the scattering diagrams in at least two regions of the spectrum. The errors, which are typical of the known X-ray devices and which are due to the nonreproducability of the measurement conditions due to the drift of electric parameters of the instrument, and errors in defining angular coordinates under repeated data acquisition. The reduction of the time it takes to make such measurements and the enhancement in the efficiency of such measurements are also thus achieved.

Figure 1:
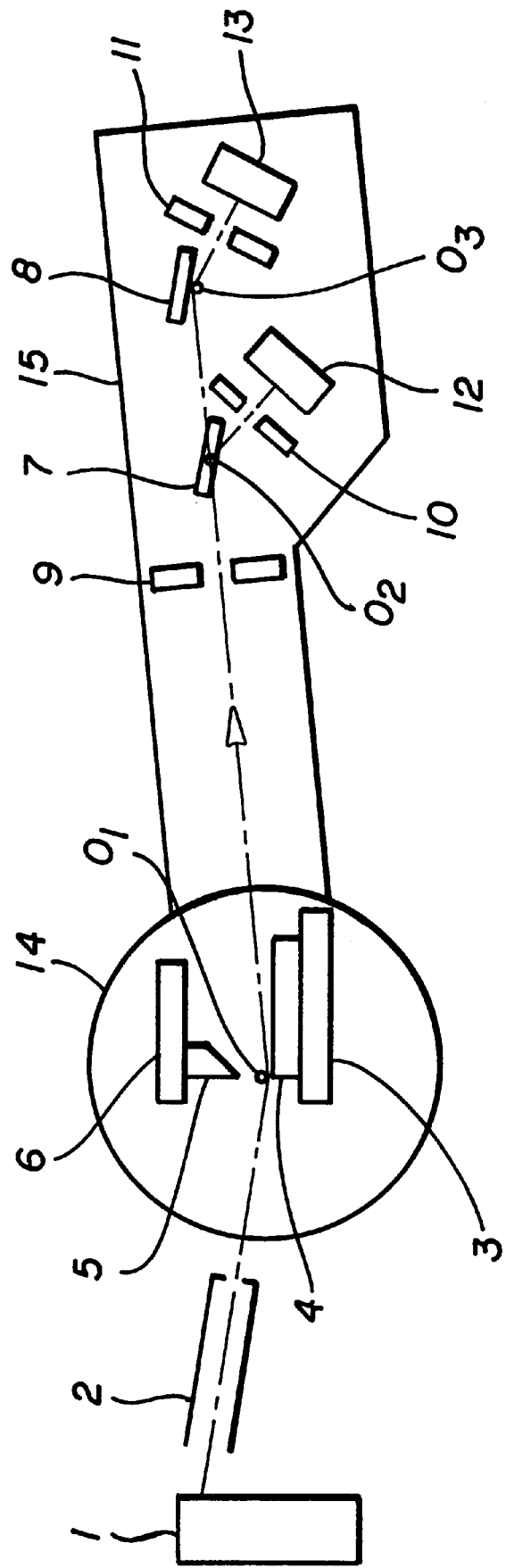
FIG. 1 illustrates a general view of the measurement scheme for an X-ray reflectometer.

The measurement scheme of the reflectometer includes the source of polychromatic X-ray radiation (X-ray tube) 1; X-ray collimator 2; holder 3 of a sample 4; collimating screen 5; device for a linear transmission 6; monochromators 7,8; the slits 9–11; the detectors 12,13; the base 14; the steering support 15. The sample 4 is fixed in the holder 3 mechanically or by means of a vacuum suction. The collimating screen 5 is fastened in the linear transmission device 6 that provides adjustment of width of a gap between surface of the sample 4 and edge of the collimating screen 5. For the monochromator 7 and the detector 12, together with the slit 10, the feasibility is provided of independent rotation in the measurement plane around axis $O_2$, and for the monochromator 8 and the detector 13, together with the slit 11, around axis $O_3$. The monochromator 7 which is the first in the path of an X-ray beam is made in the form of a thin plate of pyrolytic graphite. Thickness of the plate is optional in respect of the material of the X-ray tube anode. For a copper anode, for example, thickness is within the range of 50–100 micron. The detectors 12 and 13 represent the combination of scintillator plus photomultiplier. In the body of detectors the preamplifiers of photomultiplier pulses are placed. The axes $O_1$, $O_2$, $O_3$, and the slit 9 are located along one line. The X-ray beam width was varied by means of controlling the lengths of an output slit of the collimator 2 and the slit 9. The angular rotation of the base 14 and the support 15 was measured by a series-produced goniometer (not shown in FIG. 1) which provides continuous or stepwise motion of base 14 and support 15 around axis $O_1$ with minimal discrete step not higher than 0.0050. The path of the X-ray beam is shown by a thin line with arrow.

Figure 2:
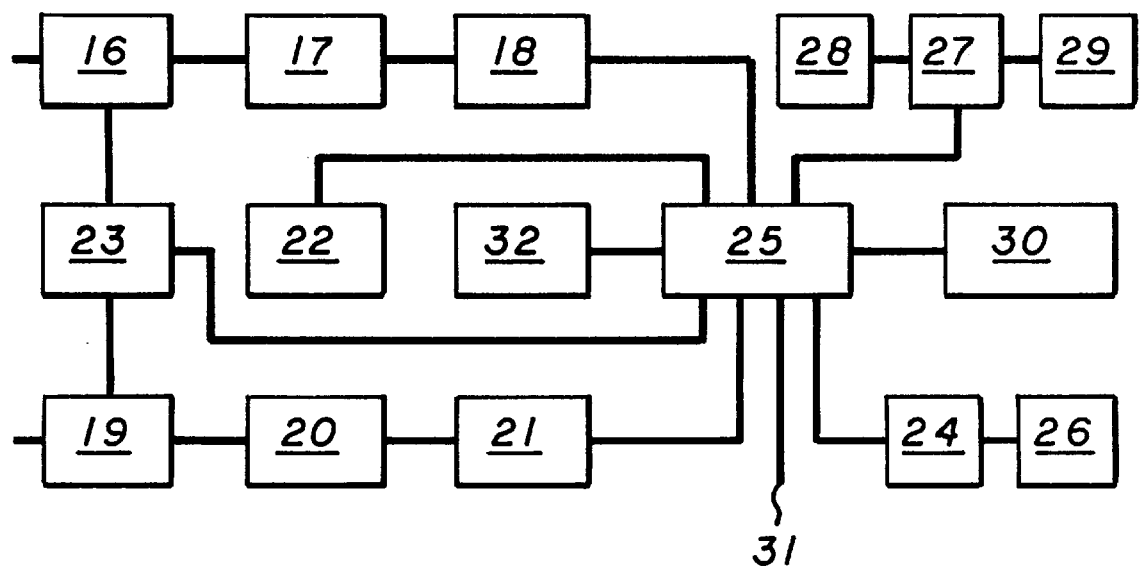
FIG. 2 is the block-scheme of the control and processing system.

The electron system of control and processing of the measurement data contains the first processing channel which includes: amplifier 16, discriminator 17 of the pulse amplitude, pulse counter 18; the second processing channel: amplifier 19, discriminator 20 of the pulse amplitude, counter 21, power supply blocks 22–24, processor 25, electromechanical device 26; pulse shaper 27; angular sensors 28,29, personal computer 30, communication line 31, electromechanical shutter 32 (FIG. 2). The elements 16–18 and 19–21 form two independent processing channels for the pulses which are generated by the detectors 12 and 13, respectively. The independent power block 23 provides for the stabilized low voltage for the electron schemes, the power block 22, high voltage for the detectors 12 and 13, the power block 24, the reversible voltage of an electromechanical device 26 with the help of which one provides continuous or stepwise rotation of the base 14 and the arm support 15 around axis $O_1$. The angular sensors 28 and 29 comprise the light diode-photodiode pairs separated by a transparent disc (not shown in FIG. 1) for which a feasibility is provided to rotate around axis $O_1$ simultaneously with the arm support 15. Over the disc circumference the blackened strips are deposited with constant angular step. The electromechanical shutter 32 is mounted in the protection body of a source of the polychromatic X-ray radiation 1. The personal computer 30 is connected with the control system through the processor 25. The coupling of the processor 25 with the power block of the polychromatic X-ray radiation source 1 is provided through the communication line 31. The data storage and the assembly control are executed by the processor 25 with the extended memory of no less than 64 kb.

Before starting measurements the X-ray reflectometer is tuned to the working spectral regions. When we use an anode made of one chemical element (Fe, Co, Ni, Cu, Mo, Ag) or their combination, the spectral ranges are chosen in such a way that they should contain the most intensive typical lines $K_\alpha$ and $K_\beta$ of the anode material. For this purpose the arm support 15 is turned so that the center of the slit 9 coincides with the direct beam axis. Monochromator 7 is turned to the Bragg angle $\theta_1$ over the axis $O_2$, for example for characteristic line Cu $K_\alpha$. The detector 12 and the slit 10 are turned by to the double Bragg angle $2\theta_1$. Monochromator 8 is turned to the Bragg angle $\theta_2$ over the axis $O_3$ for the line Cu $K_\beta$ and detector 13 and slit 11 are turned to a double Bragg angle $2\theta_2$. By angular tuning of the elements 7–13 one gets the maximum intensity registered by detectors 12 and 13. The window width and the lower threshold of the pulses coming through the discriminators 17,20 are chosen to provide the maximum value of the ratio effective signal/noise. After the tuning the sample 4 is put in the position where its edge coincides with the axis $O_1$ (see FIG. 1), and is at a given distance from the edge of the screen 5 (e.g., 30–50 $\mu$m). This allows one to maintain a fixed divergence of the reflected beam coming to the monochromators 7, 8 through the slit 9.

When measuring the angular dependence of the coefficient of X-ray reflection, the X-ray reflectometer is operating as follows. The operator inputs into the computer 30 the data related to measurement conditions: the initial angular point for the sample $\theta_o$; the current angular coordinates of the sample 4 and the slit 7 $\theta_{c1}$ and $\theta_{c2}$, respectively; the angular step between the measurements of the sample $\theta_s$; the number of angular points N; the duration of the measurement time $t_i$ in the angular point; high voltage at the X-ray tube $U_1$ and photomultiplier—$U_2$; the tube current I. By command from the computer 30 the data are transferred to the processor 25, and then the operation becomes autonomous. Processor 25 transmits through the line 31 the codes for setting the parameters to the power supply of polychromatic radiation 1 and the power supply 22 which provides the given voltage at the detectors 11,13 during the time period $T_{cT}$. After a lapse of time ($T_{cT}$) the processor 25 gives a command to the power supply block 24, and the electromechanic device 26 is turned on. This device ensures independent angular turns of the sample holder 14 and the arm support 15. During the turn of the holders 14 and the angular sensors 28 and 29 read the angular marks that are transferred through the pulse former to the processor 25. The turning is interrupted by switching off the power supplied to the electromechanical device 26 at the moment when the N-th cycle is completed.

When the initial angular position is fixed the sample plane 4 and the slit 9 are turned at negative angles ($-\theta_w$ and $-2\theta_1$) with respect to the axis of the beam incident onto the sample through the slit formed by the edge of the sample 4 and the screen 5. Then by the command transmitted from processor 25 to the electromechanical device 26 via the power supply block 24 the rotation units of the holder 14 and arm support 15 are mechanically coupled with the help of a reducer. The reducer ensures the angular shift of the sample 4 and the slit 9 in the 1:2 ratio. The preparation to the measurement procedure ends with the command coming through the block 24 to the electromechanical shutter 32. The shutter opens the output window of the X-ray polychromatic radiation source 1.

Figure 3:
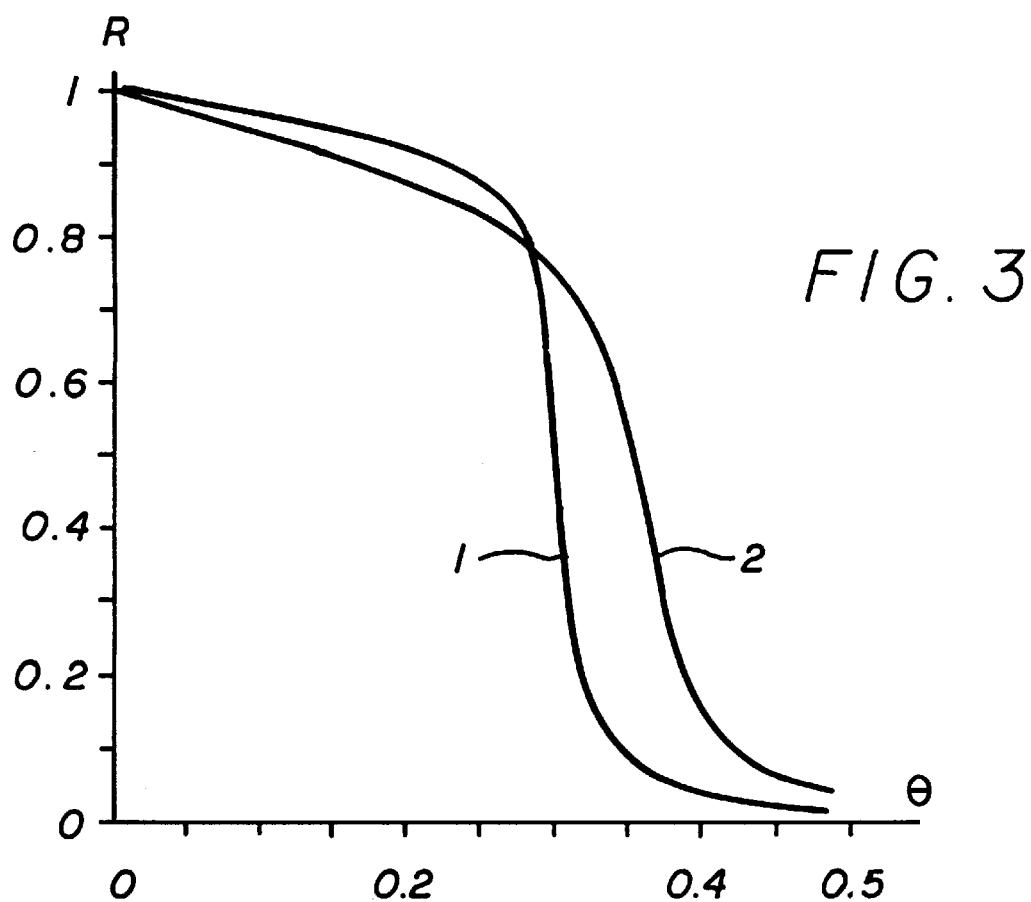
FIG. 3 depicts angular dependencies of the coefficient of the X-ray reflection, $R(\theta)$, from the sample surface in two narrow spectral regions with energies $E_1$ (curve 1) and $E_2$ (curve 2), for the case $E_1 > E_2$.

After the time $t_1$ (the time delay) the control commands are transferred from the processor 25 to the pulse counters 18, 21, and open their inputs for the time period $t_i$. During this time the pulse counters 18 and 21 register the number of pulses coming from the detectors 12 and 13 via the preamplifiers 16,19 and discriminators 17,20. When the measurement time is finished the processor 25 gives the command blocking the inputs of the pulse counters 18 and 21. The power supply block 24 is fed by the working voltage at the device 26. The data from the pulse counters 18, 21 is read by the processor 25, and their registers are nulled. While turning the mechanically coupled holder 14 and arm support 15 the processor 25 registers the pulses coming from the detector of the angular shifts of the angular sensor 28. When $\theta_s/\theta_{min}$ pulses have arrived (this corresponds to turning of the sample 4 by an angle $\theta_s$, and the slit 9 turning by an angle $2\theta_s$), the processor 25 generates a command to the power supply block 24 to switch off the working voltage at the device 26. The processor gives a command to open inputs of the pulse counters 18 and 21 for the time $t_1$. The considered cycle is repeated N–1 times. Upon completing the N-the measurement cycle the processor 25 transmits to computer 30 a message about ending the data measurements. The data stored by the processor are transmitted to the computer 30 and displayed at the computer monitor (see FIG. 3). Then the control code asks confirmation for one of the variants of the continuation: storing the data in the memory, repetition of the cycle, quit of the code.

The maximal measurement error in the reflection coefficients $R_1$ and $R_2$ at glancing angle $f=\theta_x$ consists of the following items:

$dI_1$, the error of measuring the angular coordinate of the X-ray reflected beam;

$dI_2$, the error of measuring the angular coordinate of the primary beam;

$dI_3$, the counting error due to the high voltage and X-ray tube current drift;

$dI_4$, the counting error due to the drift of the parameters of the electron pulse processing channel;

$dI_5$, $dI_6$, the statistical errors in counting the pulses of the incident and reflected beams, respectively.

In a general case the total measurement error is also the function of the glancing angle $\theta_x$ and the measurement time $t_i$. At a fixed $\theta_x$ and $t_i$ the total error $E_s$ may be written in the form:

$$E_s = \sum_{i=1}^{i=6} dI_i(\theta_x, t) \qquad (2)$$

In the case of subsequent measurements made with the help of the device [3] the geometrical items $dI_1$, $dI_2$ of the total error $E_s$ are doubled, since it is necessary, when evaluating the ultimate error, to consider the most unfavorable situation. The counting errors $dI_3$, and $dI_4$, associated with the drift of the electrical parameters, grow with the increase in the duration of the measurement cycle $T_r$, approximately proportional to square root of $T_r$. In a general case the $T_r$ is the sum of four terms: the time of tuning $t_a$, the time of defining the angular coordinates $t_k$; the time of fixing and replacing the sample $t_c$, and the time of measurement $t_m$. If the claimed device is used for parallel measurements in two spectral ranges then the duration of the measurement cycle contains only one term $t_m=T_r$, i.e. the drift time and the related errors are minimal.

The only component which may grow in a parallel measurements made with the help of a claimed device is the statistical error in counting of the pulses. This is conditioned by partial absorption of the radiation while coming through the monochromator 7. If one uses as a monochromator a thin plate made of 70 $\mu$m thick pyrolitic graphite, there is observed a 23% decrease of characteristic Cu $K_\alpha$ radiation. The integral reflection coefficient is decreased by not more than 10–20%. This results in approximately $\leq$14% increase in the mean-square deviation, which may be eliminated either by proportional increase of the power of the X-ray source or by increasing the time of the data accumulation. Under the increase in the measurement time an additional error due to the drift of the electrical parameters is a priori smaller than the error in a subsequent measurement cycles, since the total time $T_r$ does not contain the components $t_a$, $t_k$, and $t_c$ and the time of repeated measurements. In contrast to other known crystals-monochromators based on Si, $SiO_2$, Ge, LiF, a pyrolytic graphite has a minimum linear attenuation coefficient $\mu$ within the wavelength range 0.05–0.2 nm. The mentioned ranges are most frequently used in the X-ray reflectometry. Under noted thickness and 1 $cm^2$ area the above mentioned pyrographite still well preserves the plate geometrical form. When tuned to the Bragg angle the coefficient of secondary extinction for the pyrolytic graphite, as a rule, exceeds the linear attenuation coefficient. That is why its application as a first monochromator in both measurement channels of the reflectometer turns to be optimal to get the minimal statistical error in counting the quanta.

The described X-ray reflectometer may be modified to achieve other advantages both in grazing angle (X-ray optics) and standard diffractometry modes.

1. Tuning both monochromators 7, 8 to the same wavelength X-ray reflection coefficient may be increased due to diminishing shielding effect of surface layer.

2. Tuning both monochromators to the same wavelength and choosing as a second monochromator a semitransparent plate of pirolitic graphite one may consider it as single monochromator and install in a row the third pair of monochromator and detector along the way of measured X-ray beam. Working with the three detectors simultaneously allows substantially increase dynamic range of measured X-ray signal.

3. Diffracting X-rays from monochromators 7, 8 simultaneously in a single large area detector one may monitor intensity of broadband spectra transmitted through the semi-transparent monochromators.

From the foregoing detailed description, it will be evident that there are a number of changes, adaptations and modifications of the present invention, which come within the province of those skilled in the art. However, it is intended that all such variations not departing from the spirit of the invention be considered as within the scope thereof as limited solely by the claims appended hereto.

REFERENCES

1. P. Croce, L. Nevot, B. Pardo. Contribution al'etude des couches mincesss par reflexion speculaire de rayons X. Nouv. Revue d'Optique Appliquee, v.3, no 1, 37–50 (1972).
2. O. Renner. Density Measurements of Thin Germanium Films by Total Reflection of X-Rays. Czechoslovak Journal of Physics, v.B22, 1007–16 (1972).
3. The New Siemens X-Ray Reflectometer. A Tool with Outstanding Capabilities. Siemens Analytical Application Note N 337, Maerz 1 (1994).

What is claimed is:

1. An X-ray reflectometer for analyzing characteristics of a material utilizing reflected radiation, the X-ray reflectometer comprising:
   (A) an X-ray radiation source, the source being adapted to emit an incident beam of polychromatic radiation;
   (B) a base, the base being adapted to support a material, the material being supported in the incident beam of polychromatic radiation, wherein the material reflects the incident beam of polychromatic radiation producing a reflected beam of polychromatic radiation, the base further being adapted to rotate, wherein the angular position of the material relative to the incident beam of polychromatic radiation may be adjusted;
   (C) a support, the support being adapted to rotate relative to the material, wherein devices attached to the support may be positioned in the reflected beam of polychromatic radiation;
   (D) at least a first and second monochromator attached to the support, the first and second monochromators being positionable in the reflected beam of polychromatic radiation, the first and second monochromators being adapted to produce a monochromatic beam of radiation when positioned in a polychromatic beam of radiation; and
   (E) at least a first and second detector attached to the support, the first detector being positionable in the beam of monochromatic radiation produced by the first monochromators, the second detector being positionable in the beam of monochromatic radiation produced by the second monochromator, the first and second detectors being adapted to detect monochromatic radiation.

2. The X-ray reflectometer of claim 1 wherein at least one of the monochromators comprises pyrolitic graphite.

3. The X-ray reflectometer of claim 1 wherein the base is adapted to rotate around a first axis, wherein at least one of the monochromators is adapted to rotate around a second axis, the second axis being substantially parallel to the first axis.

4. The X-ray reflectometer of claim 1 wherein the base is adapted to rotate around a first axis, wherein at least the first monochromator and first detector are adapted to rotate around a second axis the second axis being substantially parallel to the first axis.

5. The X-ray reflectometer of claim 1 wherein the base is adapted to rotate around a first axis, wherein the support is also adapted to rotate around the first axis.

6. The X-ray reflectometer of claim 1 further comprising a collimator positioned between the X-ray radiation source and the material.

7. The X-ray reflectometer of claim 1 further comprising a collimating screen attached to the base.

8. The X-ray reflectometer of claim 1 further comprising a control system, the control system being adapted to control the operation of the X-ray reflectometer.

9. The X-ray reflectometer of claim 8 further comprising a processing system, the processing system being adapted to collect and analyze data from the first and second detectors.

10. A method of analyzing material using X-ray radiation, the method comprising the following steps:
   (A) emitting an incident beam of polychromatic radiation from an X-ray radiation source;
   (B) placing a material in the incident beam of polychromatic radiation;
   (C) rotating the material relative to the incident beam of polychromatic radiation to produce a reflected beam of polychromatic radiation;
   (D) providing a support with at least a first and second monochromator and a first and second detector;
   (E) rotating the support relative to the material, wherein the first and second monochromators are placed in the reflected beam of polychromatic radiation, wherein the first and second monochromators both produce a beam of monochromatic radiation;
   (F) measuring the beams of monochromatic radiation produced by the first and second monochromators using the first and second detectors.

11. The method of claim 10 further comprising the step of rotating the first and second monochromators relative to the reflected beam of polychromatic radiation.

12. The method of claim 10 further comprising the step of rotating the first and second detectors relative to the first and second monochromators.

13. The method of claim 10 wherein the material is rotated relative to an axis, wherein the support is also rotated relative the axis.

* * * * *